United States Patent [19]
Kato

[11] Patent Number: 5,888,525
[45] Date of Patent: Mar. 30, 1999

[54] WATER-PROOF DEODORIZING, BEDSORE-PREVENTING SHEET AND METHOD FOR MANUFACTURING THE SAME

[75] Inventor: Taro Kato, Iwate, Japan

[73] Assignee: Kitakamiscishi Kabushiki Kaisha, Japan

[21] Appl. No.: 916,520

[22] Filed: Aug. 22, 1997

[30]   Foreign Application Priority Data

Dec. 9, 1996  [JP]  Japan .................................... 8-342403

[51] Int. Cl.$^6$ ............................ A61K 9/70; A61K 33/26; D06M 10/06; D06M 23/00
[52] U.S. Cl. ......................... 424/402; 424/443; 424/647; 424/648; 428/275
[58] Field of Search .................................. 424/402, 76.5, 424/76.6, 76.9, 647–48, 443; 428/307.7, 308.8, 312.2, 503, 508, 509, 511, 67–68, 74, 142–43, 195, 208, 235–36, 245, 248, 254, 264, 274, 275; 427/2.13, 2.31

[56]                References Cited

U.S. PATENT DOCUMENTS 4,891,215  1/1990  Kato .
4,900,765  2/1990  Murabayashi et al. .
5,582,820  12/1996  Yamamoto et al. .

*Primary Examiner*—Edward J. Webman
*Attorney, Agent, or Firm*—Rogers & Killeen

[57]                 ABSTRACT

The present invention proposes a water-proof deodorizing, bedsore-preventing sheet that can not only eliminate the bad smell from the wastes of bedridden sick persons but also prevent the bedsore or its worsening and a method for manufacturing the same. The present invention gives such a manufacturing method that the sheet-shaped deodorizing material D obtained by allowing a sheet-shaped member made of a cellulose-based substance to contain ferrous sulfate which is subsequently oxidized into basic ferric sulfate is coated with the permeable film 1, whose fringes are partially sealed subsequently.

10 Claims, 1 Drawing Sheet

WATER-PROOF DEODORIZING, BEDSORE-PREVENTING SHEET AND METHOD FOR MANUFACTURING THE SAME

BACKGROUND OF THE INVENTION

1. Field of the Invention

The present invention relates to a water-proof deodorizing, bedsore-preventing sheet wherein its sheet-shaped deodorizing material obtained by allowing a sheet-shaped member made of a cellulose-based substance to contain tri-valent iron ions is coated with a permeable film and then heated and sealed.

2. Description of the Related Art

Conventionally, a variety of proposals have been made and put to practical use for the mats and beds which are expected to prevent or inhibit the bedsore of bedridden sick persons, but few of them have taken into account the deodorizing of the wastes of those sick persons.

That is, those conventional mats and beds are generally charged with air or liquid to facilitate the moving of bedridden sick persons so that their skin conditions in contact with the mats or beds may be improved, thus preventing bedsore or inhibiting its further worsening. Some of those mats and beds have activated carbon therein for deodorizing, which alone, however, is not enough to effectively deodorize the bad smell from the ammonia contents contained in the feces and urine.

With this, it is well expected to develop useful sheets that not only can eliminate the bad smell from the wastes of bedridden sick persons but also can prevent the bedsore itself or inhibit its further worsening.

SUMMARY OF THE INVENTION

In consideration, such problems of the prior above-mentioned above, the present invention proposes such water-proof deodorizing sheets that not only can eliminate the bad smell from the wastes of the bedridden sick persons but also can prevent their bedsore or inhibit its further worsening.

A water-proof deodorizing, bedsore-preventing sheet according to the present invention aimed at the solving of those problems features such a construction that its sheet-shaped deodorizing material obtained by allowing a sheet-shaped member made of a cellulose-based substance to contain ferrous sulfate which is subsequently oxidized into basic ferric sulfate is coated with a permeable film and then this film's fringes are heated and sealed. The method for manufacturing this sheet also features such process that the sheet-shaped member made of cellulose-based substance is poured with a ferrous sulfate solution or dipped into it which is subsequently oxidized into basic ferric sulfate by heating or at room temperature, and then dried into sheet-shaped deodorizing material which is subsequently coated with a permeable film and then heated and sealed.

The inventor of the present invention conducted a variety of research to solve those problems and has come with results that the sheet-shaped deodorizing material obtained by allowing a sheet-shaped member made of a cellulose-based substance to contain ferrous sulfate which is subsequently oxidized into basic ferric sulfate can be coated with a permeable film whose fringes are subsequently heated and sealed, to act as an effective water-proof deodorizing sheet that can eliminate the bad smell from the feces and urine given thereon and also prevent the bedridden sick persons from getting bedsore or inhibit its further worsening.

Originally, the above-mentioned water-proof deodorizing sheet is based on the confirmation by study that a combination cellulose and basic ferric sulfate has powerful deodorizing effects, which are surmised to come from the bond of the hydroxyl groups of the cellulose and the tri-valent iron ions of basic ferric sulfate. The inventor of the present invention had earlier proposed such deodorizing material effective in the deodorizing of the bad smell from the wastes of human beings and animals that contains tri-valent iron ions in its cellulose-based substance and the member formed from this substance and successfully obtained the patent right (Japanese Patent Laid-open Pub. No. 1642383).

That is, the coordinate bond between the tri-valent iron ions of basic ferric sulfate and the hydroxyl groups of cellulose is surmised to catalyze the oxidization of the smelling components by the oxygen in the air, thus decomposing ammonia causing the bad smell of wastes into nitrite and water and also hydrogen sulfide, also causing the bad smell, into water and sulfur. Moreover, even after its sheet-shaped deodorizing material is coated with a permeable film and then heated and seated, the water-proof deodorizing sheet according to the present invention formed from that would not lose its deodorizing effects and also be provided with an water-proof feature, so that even if exposed to water, it does not allow iron components to be drained. With this, therefore, this sheet, if placed between a mattress and a bed sheet, will not allow the iron components contained in its sheet-shaped deodorizing material to be drained onto the mattress or bed sheet even when sick persons urinate onto it.

Also, it is proved that use of the above-mentioned water-proof deodorizing sheet would prevent sick persons in a long-time bedridden state from getting bedsore or inhibit its further worsening. The reason is not clear but surmised It ammonia in the urine is decomposed into nitrite ions and water, so that the ammonia content, strongly alkaline, does not remain on the skin of the sick persons nor affect it.

As the permeable film employed in the present invention is preferable, e.g. a commercially available product LH00-02 of Tokuyama Co., Ltd., in which permeable polyethylene films are laminated onto a nonwoven fabric. Also, as the sheet-shaped member, which is also made of cellulose, is preferable cotton cloth, cotton nonwoven fabric, cellulose regenerated fabric cloth, cellulose regenerated nonwoven fabric, cellulose pulp nonwoven fabric, or paper towel base fiberboard.

DESCRIPTION OF THE PREFERRED EMBODIMENTS

Figure 1:
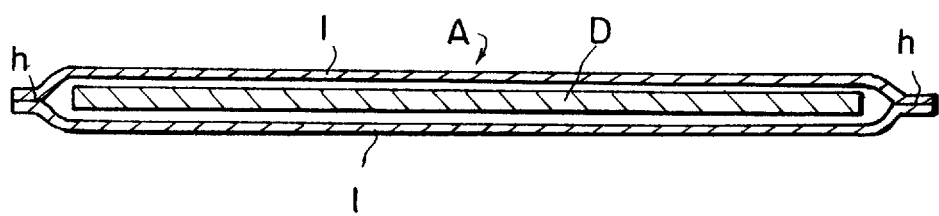
FIG. 1 is a cross-sectional view of an exemplified water-proof deodorizing, bedsore-preventing sheet according to the present invention.
Figure 2:
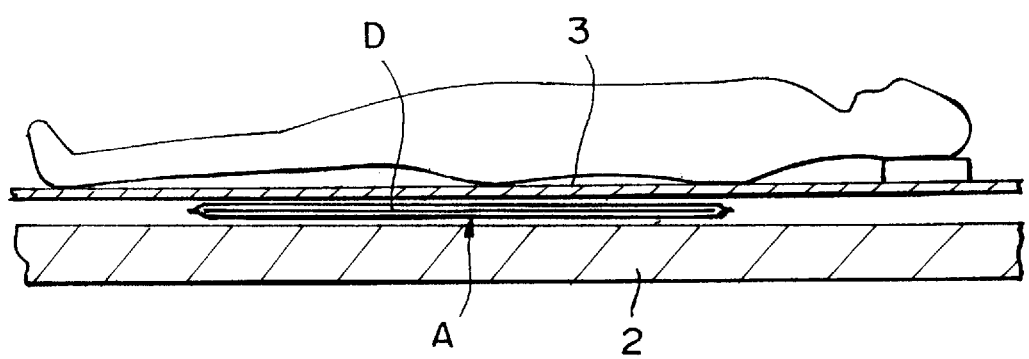
FIG. 2 is a cross-sectional view of the exemplification shown in FIG. 1.

An embodiment of the present invention will hereinafter be described.

(1) Preparation of sheet-shaped deodorizing material

As much as 150 g of ferrous sulfate, $FeSO_4 \cdot 7H_2O$, is diluted with water into a total volume of 1000 liters of ferrous sulfate solution. Thus prepared ferrous sulfate solution is applied by a roll coating machine onto paper towel base fiberboard (basis weight: 47 g/m2, width: 850 mm) by as much as 80 ml for each 1 m2 of this paper. Thus obtained paper towel base fiberboard is heated and dried to a 10% water content and then cut into sheet-shaped deodorizing material D having a width of 810 mm and a length of 910 mm.

(2) Preparation of water-proof deodorizing sheet

The sheet-shaped deodorizing material D prepare at step (1) above is coated with a permeable film 1 (width: 850 mm, length: 950 mm) and then its four sides are heated and sealed at its portions h, to provide a water-proof deodorizing, bedsore-preventing sheet A.

(3) Observation of deodorizing effects by water-proof deodorizing, bedsore-preventing sheet A, soiling of bed sheets, beds, etc. by the drainage, due to urination, of iron components contained in deodorizing material, and worsening of bedsore.

The water-proof deodorizing, bedsore-preventing sheet A prepared at step (2) above was set between a mattress 2 and a bed sheet in such a manner as to be held to the hips of 20 bedridden elderly persons for one month. The nurse smelled no feces or urine and also observed no browning of the bed sheet 3 or the mattress 2 by iron-component drainage. Four of five patients suffering from bedsore out of the 20 elderly persons were also clearly observed to be prevented from worsening of bedsore.

As can be seen from the above description, the present invention provides a manufacturing method wherein the sheet-shaped deodorizing material obtained by allowing a sheet-shaped member made of a cellulose-based substance to contain ferrous sulfate which is subsequently oxidized into basic ferric sulfate is coated with a permeable film, whose fringes are subsequently heated and sealed. Thus made sheet-shaped deodorizing material, when placed between a mattress and a bed sheet, deodorizes the smell from the wastes, if any, and prevents the browning of those bedclothes because of the drainage of the iron components and also the transfer of the bad smell to the mattress, largely decreasing the required number of time of cleaning. Also, this kind of deodorizing sheet was clearly observed to stop the further worsening of the bedsore of those elderly persons.

The water-proof deodorizing, bedsore-preventing sheet according to the present invention, therefore, can be used for bedridden elderly persons as mentioned above, not only to solve the problems of the bad smell from the wastes but also to largely ease the labor of, e.g. nursing of those persons.

Also, the present invention proposes an easy and inexpensive method of manufacturing the above-mentioned water-proof deodorizing, bedsore-preventing sheets that comprises the following three steps:

(1) Pour a solution of ferrous sulfate onto a sheet-shaped member made of a cellulose-based substance or dip it into that solution.

(2) Oxidize the ferrous sulfate into basic ferric sulfate, to dry that member.

(3) Coat the member with a permeable film, to subsequently heat and seal it.

What is claimed is:

1. A water-proof deodorizing, bedsore preventing sheet including a sheet-shaped deodorizing material obtained by providing a sheet-shaped member of a cellulose-based substance containing ferrous sulfate which is subsequently oxidized into basic ferric sulfate, the sheet shaped member being coated with a permeable film, the fringes of which are sealed.

2. A water-proof deodorizing, bedsore-preventing sheet as claimed in claim 1 wherein its sheet-shaped material made of a cellulose-based substance is either cotton cloth, cotton nonwoven cloth, cellulose regenerated fabric cloth, cellulose regenerated nonwoven fabric, cellulose pulp nonwoven fabric, or paper-towel base fiberboard.

3. A method of manufacturing water-proof deodorizing, bedsore-preventing sheets including the steps of:

(a) providing a sheet-shaped deodorizing material by either (i) pouring a ferrous-sulfate solution onto a sheet-shaped member made of a cellulose based substance or (ii) dipping the member into that solution and (b) oxidizing said ferrous sulfate into basic ferric sulfate by (i) heating or (ii) drying at room temperature and (c) then coating that member with a permeable film and (d) heating and sealing the fringes thereof.

4. A method of manufacturing water-proof deodorizing, bedsore-preventing sheets as claimed in claim 1 wherein its sheet-shaped material made of a cellulose-based substance is either cotton cloth, cotton nonwoven fabric, cellulose regenerated fabric cloth, cellulose regenerated nonwoven fabric, cellulose pulp nonwoven fabric, or paper-towel base fiberboard.

5. A method of manufacturing water-proof deodorizing, bedsore-preventing sheets comprising the steps of:

(a) providing a sheet-shaped cellulose based substance;

(b) impregnating the substance with a ferrous-sulfate solution;

(c) oxidizing the ferrous sulfate in the impregnated substance into basic ferric sulfate;

(d) coating the substance with a permeable film; and (e) heat sealing the fringes of the film to enclose the impregnated substance.

6. The method of claim 5 wherein the substance in impregnated by pouring a ferrous-sulfate solution onto the sheet-shaped member.

7. The method of claim 5 wherein the substance in impregnated by dipping the substance into a ferrous-sulfate solution.

8. The method of claim 5 wherein the ferrous sulfate in the impregnated substance is oxidized into basic ferric sulfate by drying at room temperature until such time as a moisture content of about 10% is achieved.

9. The method of claim 5 wherein the ferrous sulfate in the impregnated substance is oxidized into basic ferric sulfate by heating until such time as a moisture content of between about 10% and 20% is achieved.

10. The method of claim 5 wherein the ferrous sulfate in the impregnated substance is oxidized into basic ferric sulfate having an iron concentration of about 5%.

\* \* \* \* \*